(12) United States Patent
Cleek et al.

(10) Patent No.: US 9,320,890 B2
(45) Date of Patent: Apr. 26, 2016

(54) DRUG ELUTING COMPOSITE

(75) Inventors: Robert L. Cleek, Flagstaff, AZ (US);
Edward H. Cully, Flagstaff, AZ (US);
Theresa A. Holland, Flagstaff, AZ (US);
Thomas R. McDaniel, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 12/941,839

(22) Filed: Nov. 8, 2010

(65) Prior Publication Data

US 2011/0112618 A1 May 12, 2011

Related U.S. Application Data

(63) Continuation-in-part of application No. 12/909,609, filed on Oct. 21, 2010, now abandoned.

(60) Provisional application No. 61/259,491, filed on Nov. 9, 2009.

(51) Int. Cl.
| | |
|---|---|
| *A61N 1/05* | (2006.01) |
| *A61K 47/30* | (2006.01) |
| *A61K 47/32* | (2006.01) |
| *A61K 31/56* | (2006.01) |
| *A61L 29/08* | (2006.01) |
| *A61L 31/10* | (2006.01) |

(52) U.S. Cl.
CPC ............ *A61N 1/056* (2013.01); *A61L 29/085* (2013.01); *A61L 31/10* (2013.01); *A61N 1/0568* (2013.01); *A61L 2300/222* (2013.01); *A61L 2300/608* (2013.01)

(58) Field of Classification Search
None
See application file for complete search history.

(56) References Cited

U.S. PATENT DOCUMENTS

| | | |
|---|---|---|
| 3,892,238 A | 7/1975 | Banford et al. |
| 3,926,188 A | 12/1975 | Baker et al. |
| 4,596,555 A | 6/1986 | Theeuwes |
| 4,601,893 A | 7/1986 | Cardinal |
| 5,290,271 A | 3/1994 | Jernberg |
| 5,578,069 A | 11/1996 | Miner |
| 5,605,696 A | 2/1997 | Eury et al. |
| 5,662,698 A | 9/1997 | Altman et al. |
| 6,306,428 B1 | 10/2001 | Lehmann et al. |
| 6,753,071 B1 | 6/2004 | Pacetti |
| 7,014,913 B2 | 3/2006 | Pacetti |
| 7,691,401 B2 | 4/2010 | Castro et al. |
| 7,771,413 B2 | 8/2010 | Massengale et al. |
| 2002/0138123 A1 | 9/2002 | Casas-Bejar et al. |
| 2004/0024448 A1* | 2/2004 | Chang et al. .................. 623/1.42 |
| 2005/0008673 A1 | 1/2005 | Snyder et al. |
| 2005/0107738 A1 | 5/2005 | Slater et al. |
| 2005/0113903 A1* | 5/2005 | Rosenthal et al. ............ 623/1.15 |
| 2005/0208098 A1* | 9/2005 | Castro et al. ................... 424/423 |
| 2006/0111626 A1 | 5/2006 | Rossing et al. |
| 2006/0269475 A1 | 11/2006 | Ryu et al. |
| 2006/0276885 A1 | 12/2006 | Lye et al. |
| 2007/0299491 A1* | 12/2007 | Borgaonkar et al. .......... 607/120 |
| 2008/0026034 A1* | 1/2008 | Cook et al. .................... 424/426 |
| 2008/0075833 A1 | 3/2008 | Pacetti |
| 2009/0087380 A1 | 4/2009 | Fasching et al. |
| 2009/0132031 A1 | 5/2009 | Cook et al. |
| 2009/0324676 A1 | 12/2009 | Hofmann et al. |
| 2011/0066108 A1 | 3/2011 | Geipel et al. |

FOREIGN PATENT DOCUMENTS

| | | |
|---|---|---|
| EP | 1 545 642 | 6/2005 |
| EP | 1 847 290 | 10/2007 |
| GB | 2440679 | 2/2008 |
| JP | 4-224513 | 8/1992 |
| WO | 00/25854 | 5/2000 |

* cited by examiner

*Primary Examiner* — Robert A Wax
*Assistant Examiner* — Randeep Singh
(74) *Attorney, Agent, or Firm* — Kilpatrick Townsend & Stockton LLP

(57) ABSTRACT

The present invention relates to materials having therapeutic compositions releasably contained within the materials. The materials are configured to release therapeutic compositions at a desired rate. The present invention also relates to devices incorporating the materials.

21 Claims, 14 Drawing Sheets

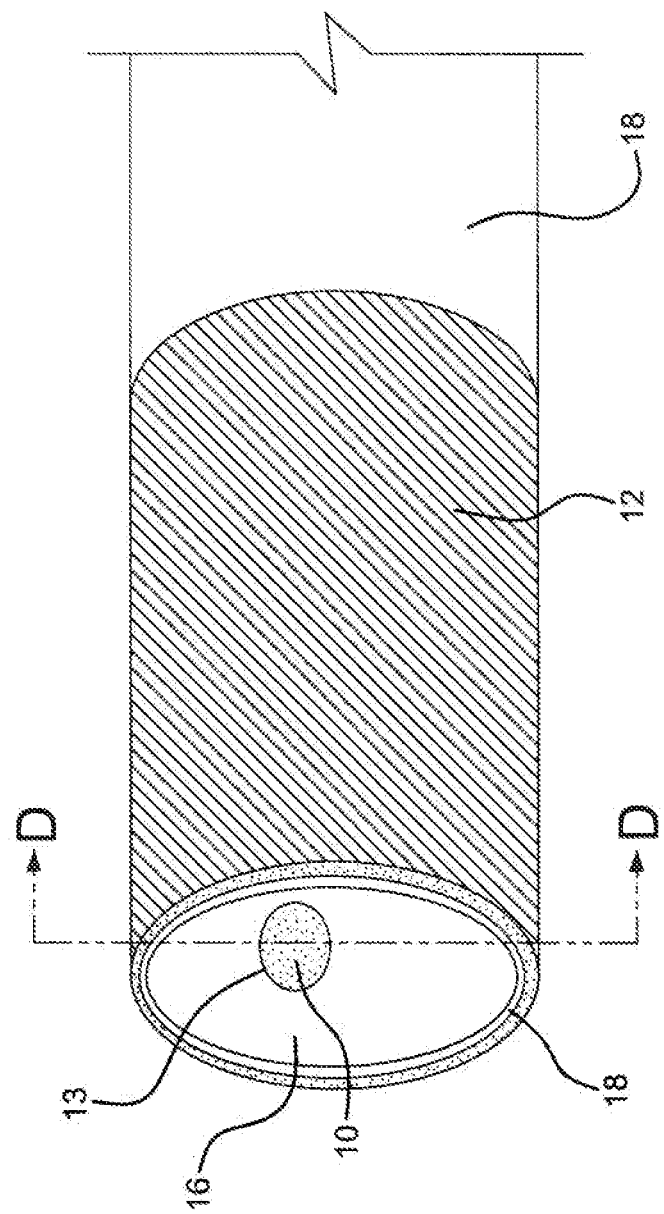

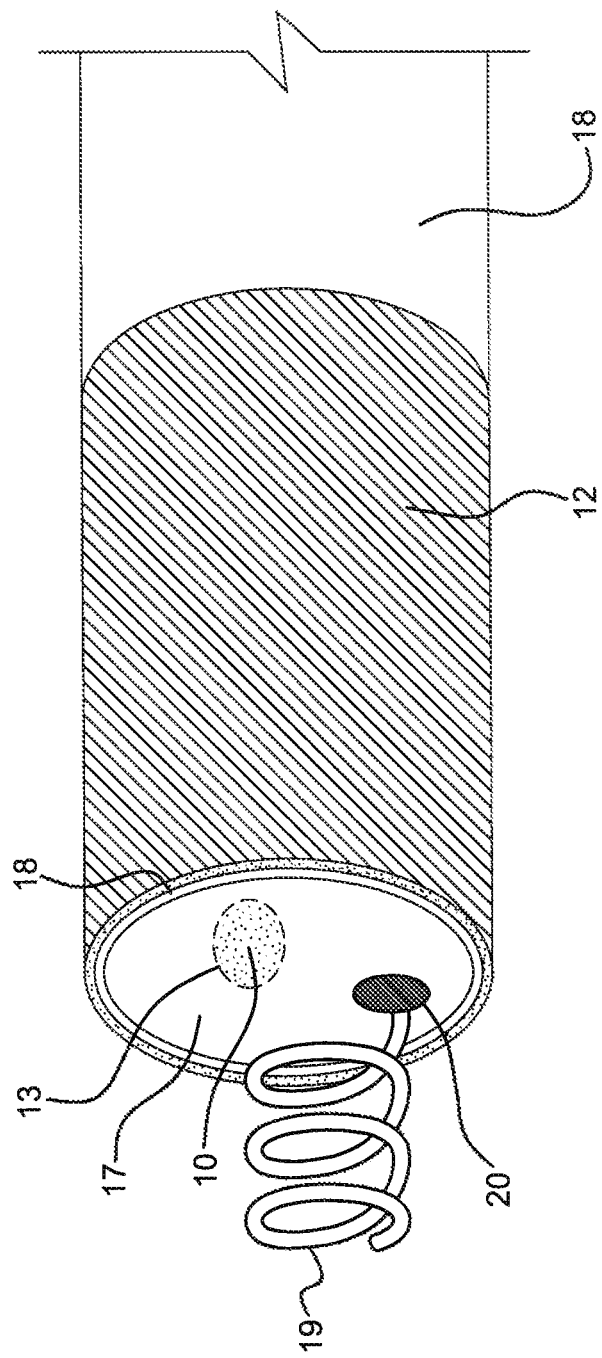

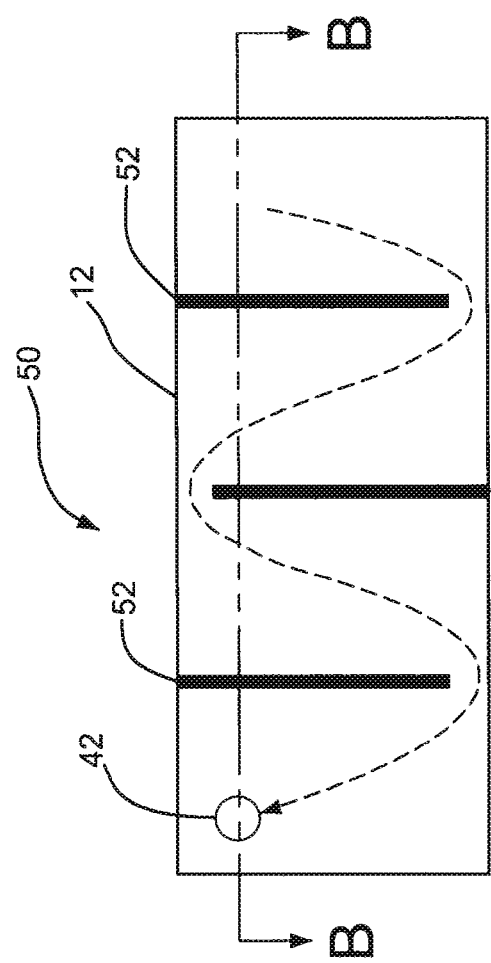
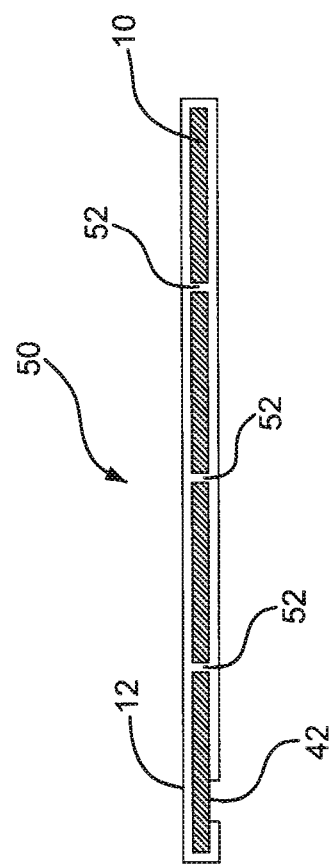
FIG. 9A
FIG. 9B

DRUG ELUTING COMPOSITE

CROSS-REFERENCE TO RELATED APPLICATIONS

This application is a continuation-in-part application of application Ser. No. 12/909,609, filed Oct. 21, 2010 now abandoned and claims priority to provisional application U.S. Ser. No. 61/259,491, filed Nov. 9, 2009.

FIELD OF THE INVENTION

The present invention relates to medical devices and materials capable of releasing a therapeutic agent.

SUMMARY OF THE INVENTION

The present invention relates to materials capable of releasing a therapeutic agent contained within the invention at determined concentrations over determined periods of time. Pathways are present within the material of the invention for therapeutic agents to traverse. The pathways extend the distance therapeutic agents contained within the invention must travel within and to exit the invention. The time taken for therapeutic agents to exit the invention is also extended by the pathways. Pathways are established in the present invention with combinations of permeable and impermeable compositions and/or structures located within the material containing the therapeutic agents. Compositions and/or structures impermeable to a selected therapeutic agent are also used as barriers to the therapeutic agent on at least portions of one or more surfaces of the invention. As a result, the therapeutic agent can only exit the invention in areas not covered, contacted, or otherwise constructed with compositions and/or structures impermeable to the selected therapeutic agent. Openings are also provided in the compositions and/or structures impermeable to a selected therapeutic agent in some embodiments of the invention.

In alternative embodiments, pathways are established in the present invention with combinations of permeable and semi-impermeable compositions and/or structures located within the material containing the therapeutic agents. Semi-impermeable compositions and/or structures serve as barriers or other impediments to movement of therapeutic agents through the invention. As a result the therapeutic agent will pass more slowly through the semi-impermeable compositions and/or structures than through the permeable compositions and/or structures.

Embodiments of the present invention allow for the tailoring of delivery of therapeutic compositions. In some embodiments such tailoring may be effected by altering the dimensions, compositions, characteristics, and placement of the impermeable or semi-impermeable compositions and/or structures without altering the starting amount or distribution of therapeutic agent present in the embodiment.

Embodiments of the present invention can be used alone or in combination with other embodiments of the invention. The invention can also be a component of a device such as cardiac pacing devices, cardiac defibrillation devices, neurostimulation devices, endoprostheses such as grafts and stent-grafts, drug delivery devices, interventional devices such as catheters and filters, diagnostic devices such as transducers, sensors, and other medical devices placed in proximity to living tissue and/or fluids targeted by one or more therapeutic agents. Embodiments of the present invention may be used in combination with medical devices placed within or on the body for short or long periods of time.

Implantable embodiments of the invention can be used to elute an anti thrombogenic drug into a specific location within the body such as proximate the prostate gland or the left atrial appendage. Prevention of blood clots in the region of the left atrial appendage could obviate the need for a left atrial appendage occluder. In this embodiment, the therapeutic composition, agent, or compound in the present invention could be incorporated into an implantable embodiment and elute a high concentration of therapeutic when implanted which is subsequently rapidly diluted when the blood is washed out into the heart and circulatory system.

Such implantable embodiments of the present invention can also be constructed to elute therapeutics over more extended periods of time.

Accordingly, one embodiment of the present invention relates to a therapeutic-releasing material comprising a first biocompatible polymeric material having at least one surface and a therapeutic agent releasably incorporated in at least a portion thereof, wherein a portion of said first biocompatible polymeric material is impermeable to said therapeutic agent, and a second biocompatible polymeric material impermeable to said therapeutic agent covering substantially all said at least one surface.

Another embodiment of the present invention relates to a therapeutic-releasing material comprising a porous biocompatible polymeric material having at least one surface, a therapeutic agent releasably admixed with a biocompatible fluoropolymeric copolymer and incorporated in pores of said porous biocompatible polymeric material, wherein a portion of said porous biocompatible polymeric material is impermeable to said therapeutic agent, and a non-porous biocompatible polymeric material impermeable to said therapeutic agent covering substantially all said at least one surface.

A further embodiment of the present invention relates to a first biocompatible polymeric material in the form of a film having at least one surface and a therapeutic agent releasably incorporated in at least a portion of said film, wherein a portion of said first biocompatible polymeric material is impermeable to said therapeutic agent, and a second biocompatible polymeric material impermeable to said therapeutic agent covering substantially all said at least one surface of said film.

Other embodiments of the present invention relate to medical devices having a therapeutic-releasing material incorporated therein. For example, one embodiment relates to a cardiac pacing or Intracardiac Cardioverter Defibrillation (ICD) leads comprising a cardiac lead element having a proximal end and a distal end, an electrically conductive connector at said proximal end, an electrode located at said distal end, at least one electrically conductive element connecting said connector to said electrode, and at least a portion of said cardiac element covered with a therapeutic-releasing material having a first biocompatible polymeric material having at least one surface and a therapeutic agent releasably incorporated in at least a portion thereof, wherein a portion of said first biocompatible polymeric material is impermeable to said therapeutic agent and a second biocompatible polymeric material impermeable to said therapeutic agent covering substantially all said at least one surface.

Another embodiment relates to an electrically conductive lead comprising a lead element having a proximal end and a distal end, an electrically conductive connector at said proximal end, an electrode located at said distal end, at least one electrically conductive element connecting said connector to said electrode, a tubular lead tip located at said distal end, and at least a portion of said lead element covered with a therapeutic-releasing material having a first biocompatible polymeric material having at least one surface and a therapeutic agent releasably incorporated in at least a portion thereof, wherein a portion of said first biocompatible polymeric material is impermeable to said therapeutic agent and a second biocompatible polymeric material impermeable to said therapeutic agent covering substantially all said at least one surface.

In each embodiment of the present invention, at least one opening can be placed in the impermeable materials and/or impermeable portions of the invention to provide a path for therapeutic agents to be released from, or otherwise travel through, the material.

BRIEF DESCRIPTION OF THE DRAWINGS

FIG. 2 illustrates a perspective view of another embodiment of the present invention.

FIG. 3 illustrates a perspective view of the embodiment of FIG. 2.

FIG. 9A illustrates an embodiment of the present invention.

FIG. 9B illustrates a transverse cross section taken at the line "B" in FIG. 9A.

DETAILED DESCRIPTION OF THE INVENTION

Figure 1:
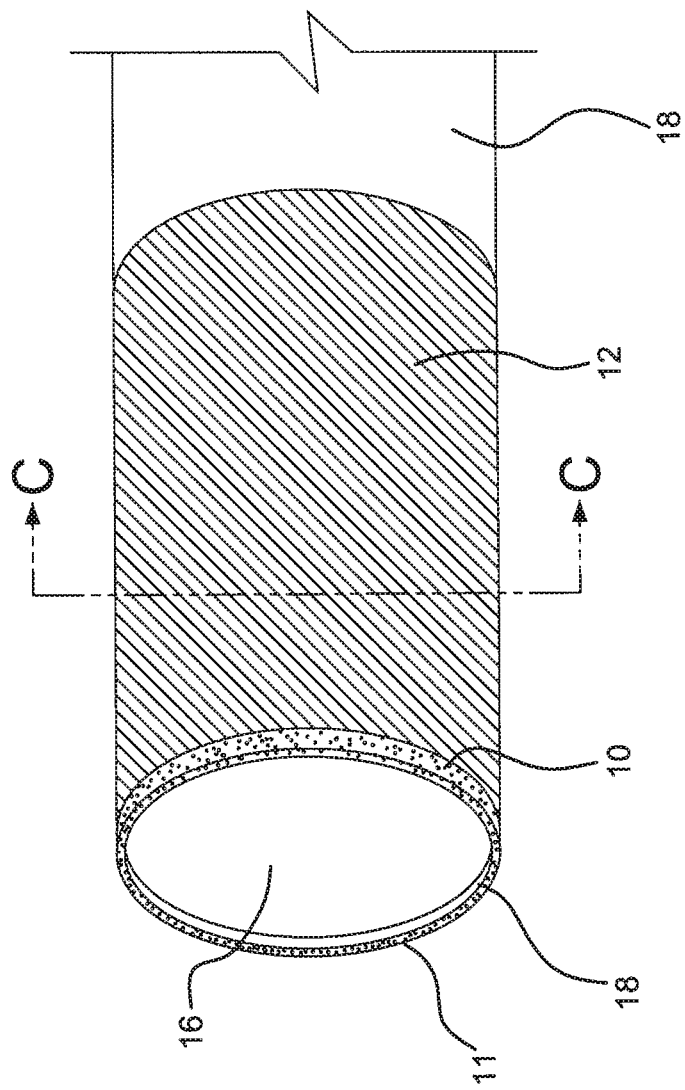
FIG. 1 illustrates a perspective view of an embodiment the present invention.

The present invention relates to materials having therapeutic compositions releasably contained within the materials. The materials are configured to release therapeutic compositions at a desired rate. The present invention also relates to devices incorporating the materials. In preferred embodiments, materials and/or constructions bar, or otherwise impede, movement of therapeutic compositions present within the material of the invention. Some embodiments have materials and/or constructions reducing, or otherwise limiting, the rate of release of therapeutic compositions from the invention, but not barring, blocking, or otherwise impeding movement of a therapeutic composition through the invention.

The rate at which therapeutic agents are released from the invention is influenced by several factors. These include the chemical composition of the components of the invention, the physical relationship of the components, the overall shape of the invention, and any openings provided in the invention. The chemical composition of the components of the invention include formulations of the therapeutic agent and materials containing the therapeutic agent, such as mass fractions, presence or absence of expedients, and the magnitude of the diffusion coefficient for the invention.

Combinations of compositions and/or structures permeable to therapeutic agents and compositions and/or structures impermeable to therapeutic agents are used in the present invention to establish a pathway along which therapeutic agents move as the agents move through and out of the invention. As a result, therapeutic agents are preferentially eluted, or otherwise released, from permeable portions of the material and not impermeable portions. In some embodiments semi-permeable compositions and/or structures can be used as partial barriers or other partial impediments to movement of therapeutic compositions through the invention.

A notable advantage of the invention is the ability to control the release rate concurrently with the total percentage of therapeutic compositions released. Some therapeutic compositions are unstable and it is not desirable to leave large or even small portions of the compositions remaining within the invention for periods of time. With more traditional approaches, the rate of release is controlled through the mixture of the therapeutic compositions and a polymer. Unlike the present invention, therapeutic compositions can remain within a conventional device permanently or for undesirable periods of time.

In addition, the invention has a variety of configurations which can influence the rate at which therapeutic agents are released from the invention. The configurations include films, sheets, rods, tubular shapes having luminal spaces, hollow or solid spherical shapes, laminates, wraps, and other shapes.

The material of the present invention includes therapeutic compositions, agents, or compounds such as small molecule drugs, large molecule drugs, medicaments, cardiovascular agents, chemotherapeutics, antimicrobials, antibiotics, anesthetics, hemostatics, antihistamines, antitumors, antilipids, antifungals, antimycotics, antipyretics, vasodilators, hypertensive agents, oxygen free radical scavengers, vitamins, antivirals, analgesics, antiproliferatives, antiinflammatories, diagnostic agents, visualization agents, angiographic contrast agents, phase contrast agents, and radiopaque agents, or thrombolytics intended to facilitate the breakup of thrombus, anticoagulants such as heparin, intended to prevent thrombosis and combinations thereof. The therapeutic composition may be an anti-inflammatory steroid such as dexamethasone sodium phosphate, dexamethasone acetate, dexamethasone, and/or beclomethasone dipropionate.

Yet other therapeutic compositions include, but are not limited to, antirestenotic drugs including, but not limited to, pimecrolimus, cytochalasin, dicumarol, cyclosporine, latrunculin A, methotrexate, tacrolimus, halofuginone, mycophenolic acid, genistein, batimistat, dexamethasone, cudraflavone, simvastatin, prednisolone, doxorubicin, bromopyruvic acid, carvedilol, mitoxantrone, tranilast, etoposide, hirudin, trapidil, mitomycin C, abciximab, cilostazol, irinotecan, estradiol, diaziquone, dipyridamole, melatonin, colchicine, nifedipine, vitamin E, paclitaxol, diltiazem, vinblastine, verapamil, vincristine, rapamycin, angiopeptin, everolimus, heat shock proteins, zotarolimus, nitroglycerin, and prednisone.

In a preferred embodiment of the present invention, a film material permeable to a therapeutic compound is impregnated or coated with a copolymer into which has been admixed the therapeutic compound. The preferred film material is an expanded polytetrafluoroethylene (ePTFE) construction. The copolymer is preferably a tetrafluoroethylene/perfluoromethylvinylether (TFE/PMVE) copolymer. The resulting coated film may become less-permeable and preferably impermeable to the therapeutic compound. In some instances the permeability of the film may not change.

In some embodiments, a material impermeable to the therapeutic composition, agent, or compound is placed on at least one surface of the therapeutic-containing, coated film material as a "capping layer" to prevent movement of the therapeutic agent or compound through or out of the invention at the location of the impermeable material. The material for the "capping layer" is preferably formed of a polymer such as a silicone composition. Depending on the embodiment, the capping layer material is applied either to a portion of the coated film material or all of the film material. The portion of the coated film material which is not covered by the capping layer material preferentially elutes the therapeutic composition, agent, or compound when exposed to fluids. The capping layer material may be applied over the coated film material after the film material is applied to a substrate.

In some embodiments, the impermeable material, be it a "capping-layer" or a coated film has at least one opening therein.

In some embodiments, the present invention is combined with a substrate in the form of a device or other construction. In these embodiments, a coated film material is applied to all or a portion of the substrate underlying the invention. The coated film material may be cut into a tape and applied by wrapping the tape around the substrate. The tape is wrapped spirally, helically and/or longitudinally around at least a portion of the substrate. An adhesive may be used as needed to adhere the spirally-wrapped layers of film. If the coated film is "capped" with a capping layer which prevents elution from the coated film construct, the capping layer may also serve as an adhesive. The coated film may be applied to the substrate with the coated side facing the substrate or facing away from the substrate. Substrates may include tubes, rods, pellets, or any other three dimensional object, including substrates which may be a component of an assembled device. Substrates may be made of metals, polymers, and the like. The substrate may be shaped or altered to form elution pathways through and out of the present invention.

As used herein, the term "bioabsorbable" refers to a physiological process in which at least a portion of a material hydrolyzes, degrades, or otherwise dissolves in living tissue or biological fluid.

As used herein, the term "permanent implant" refers to a medical device intended to be implanted in a patient for all or most of the life of the patient.

As used herein, the term "semi-permanent implant" refers to a medical device intended to be implanted in a patient for less than most of the expected life of the patient. Semi-permanent implants are often accessed following implantation for removal of the device or other procedure related to the device.

Referring to FIG. 1, coated film (10) has a therapeutic composition, agent, or compound (not shown) incorporated with a film. Coated film (10) is applied over a substrate (18). A capping layer (12) is applied over coated film (10). The capping layer (12) is either made of materials impermeable to the particular therapeutic composition, agent, or compound or constructed to be impermeable to the particular therapeutic composition, agent or compound.

In this embodiment, the substrate (18) is a tubular structure with a luminal space (16). Material of the capping layer (12) covers only a portion of the coated film material (10) thereby leaving a portion of coated film material exposed around an edge, or lip, of the substrate (18). The exposed portion of the coated film material (10) has a thickness dimension (11).

Figure 1A:
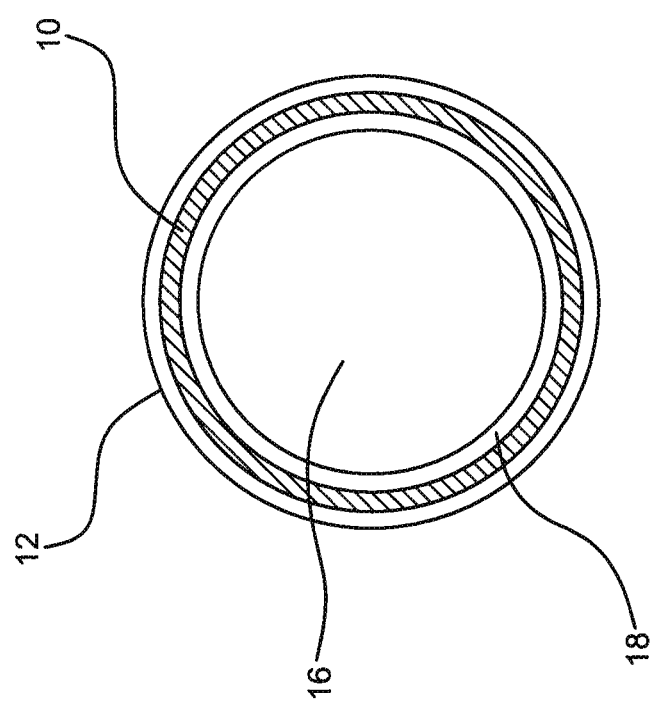
FIG. 1A illustrates a transverse cross section taken at line "C" in FIG. 1.

This embodiment is also illustrated in FIG. 1A as a transverse cross section taken at line "C" in FIG. 1 showing substrate material (18), luminal space (16), coated film material (10) and capping layer material (12).

In practice, the embodiment illustrated in FIG. 1 is placed in contact with or in proximity to a bodily tissue or fluid. Once in contact with tissue and/or fluid, the therapeutic composition, agent, or compound (not shown) contained within coated film (10) is preferentially eluted from those portions of the coated film material not covered by material of the capping layer (12). In this embodiment, for example, the therapeutic composition, agent, or compound elutes or otherwise exits the invention from an uncapped, or otherwise uncovered, edge (11) surrounding the opening of luminal space (16). The therapeutic composition, agent, or compound in the coated film material (10) may diffuse, or otherwise migrate, from portions of the coated film material (10) covered by material of the capping layer (12) and exit the invention from uncovered and exposed areas of the coated film material (10).

Another embodiment of the present invention is illustrated in FIG. 2. In this embodiment, coated film material (10) has a therapeutic composition, agent, or compound (not shown) incorporated into the film. The coated film material (10) is applied over a substrate (18). A capping layer material (12) is applied over the entire exterior surface of coated film material (10). The capping layer (12) is either made of materials impermeable to the particular therapeutic composition, agent, or compound or constructed to be impermeable to the particular therapeutic composition, agent, or compound. An opening (13) in the form of a hole is made through substrate 18, exposing coated film material (10) to the luminal space (16) of the substrate (18). A porous material may be placed over opening (13) and between the substrate (18) and coated film material (10). Additionally, this material placed over opening (13) may modulate release of a therapeutic composition, agent, or compound.

Figure 2A:
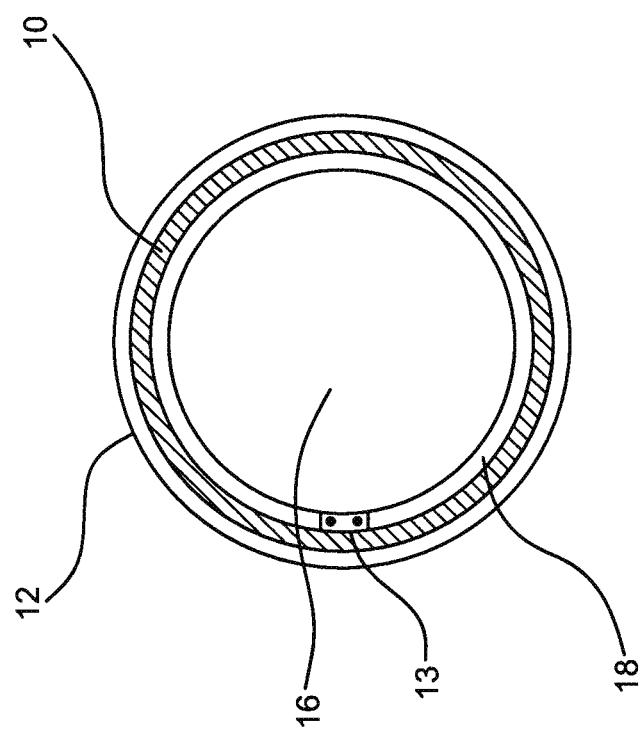
FIG. 2A illustrates a transverse cross section taken at line "D" in FIG. 2.

FIG. 2A is a transverse cross section taken at line "D" in FIG. 2 showing substrate (18), luminal space (16), coated film material (10), capping layer material (12), and opening (13).

In practice, the embodiment illustrated in FIG. 2 is placed in contact with or in proximity to a tissue or fluid. Once in contact with tissue and/or fluid, the therapeutic composition, agent, or compound in coated film material (10) preferentially elutes through opening (13) and out of luminal space (16) into surrounding fluid and/or tissues (not shown). The therapeutic composition, agent, or compound in coated film material (10) may migrate to opening (13) from portions of coated film material (10) covered by capping layer material (12) and located away from opening (13).

FIG. 3 is a perspective view of the embodiment illustrated in FIG. 2 except cover material (17) covers luminal space (16) as shown in FIG. 2. Optionally, an opening (20) can be made in cover material (17) through which tissue fixation means (19), such as a screw may be included. Additional means of tissue fixation include appropriate anchors, barbs, hooks or adhesives. The tissue fixation means can be made of metallic or polymeric materials. The metallic or polymeric materials can be bioabsorbable or non-bioabsorbable. An example of a bioabsorbable metal is magnesium. An example of a bioabsorbable polymer is polyglycolic acid commonly known as PGA.

In practice, the embodiment illustrated in FIG. 3 is anchored into tissue using tissue fixation screw (19) and the therapeutic composition, agent, or compound in coated film material (10) is allowed to preferentially elute from opening (13) into luminal space (16) and out of opening (20) into surrounding tissues and/or fluids. The embodiment illustrated in FIG. 3 may be used for implantation into the heart and other tissues as described below. For example, in cardiac leads a tissue fixation screw (19) is often placed into the septum of the right ventricle.

Figure 4:
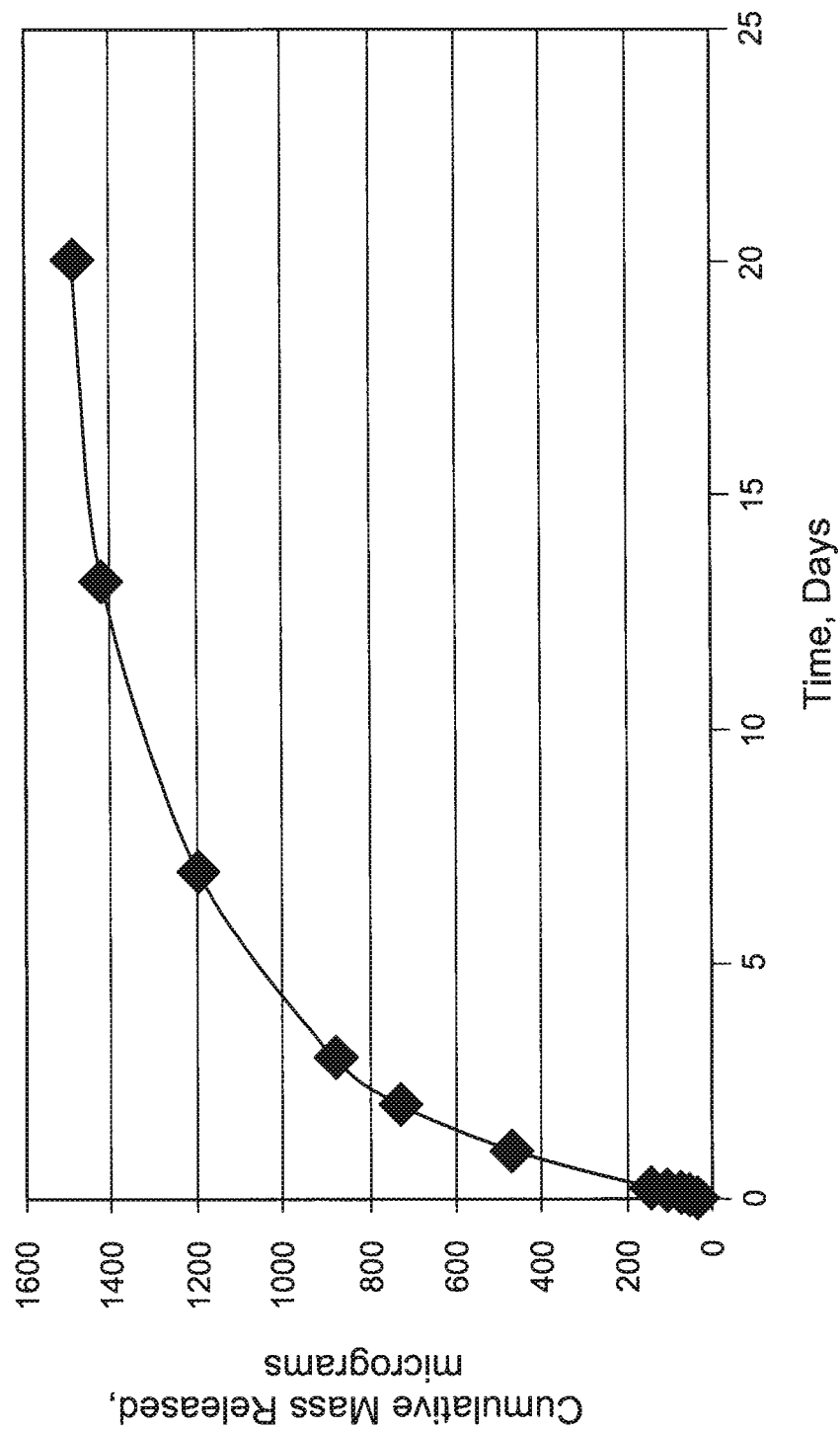
FIG. 4 is a graph.

FIG. 4 is a graph of the cumulative mass of drug released as a function of time for the embodiment described in Example 1.

Figure 5:
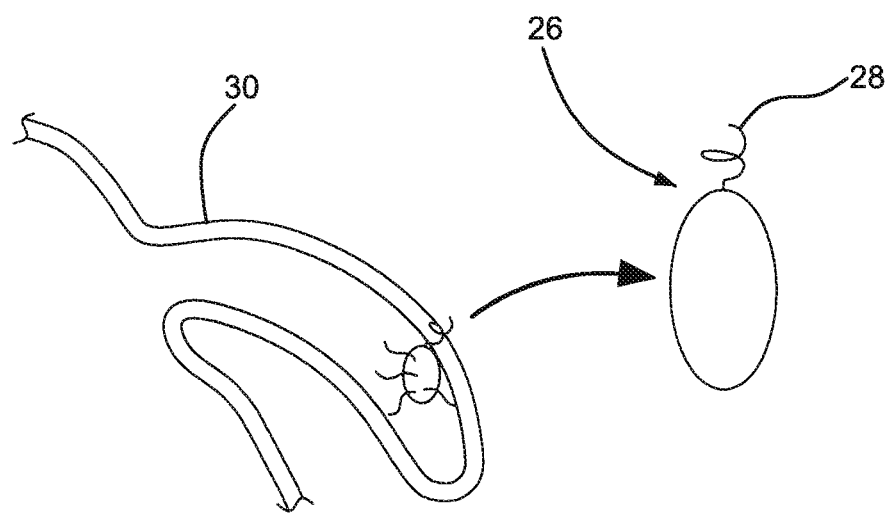
FIG. 5 illustrates an embodiment of the present invention.

FIG. 5 illustrates another embodiment of the present invention. A housing (26) includes a therapeutic eluting construction of the present invention with a means to attach the housing (26) to tissue such as a tissue attachment screw (28). Depending on the application, the housing (26) may be attached to a tissue region or anatomical location such as a left atrial appendage (30). The attachment may be permanent or semi-permanent in the event the housing (26) is subsequently removed and optionally exchanged.

Figure 7:
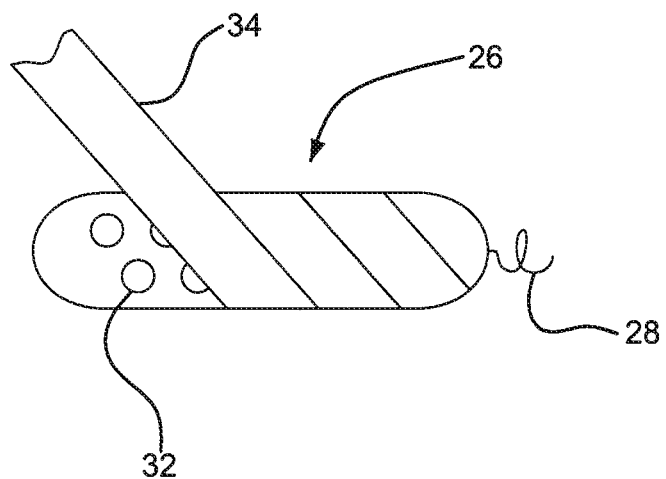
FIG. 7 illustrates an embodiment of the present invention.

The housing (26) may be incorporated in the embodiment described in Example 1. The housing (26) may be made of metallic or polymeric materials. The housing (26) is solid, hollow, or include features such as perforations (32) as illustrated in FIG. 7.

In one embodiment, both a housing (26) and tissue attachment screw (28) are made of materials which are bioabsorbable. In one embodiment, the entire housing (26) is a solid bioabsorbable material having with a therapeutic composition, agent, or compound incorporated therein. Over time, the entire housing implant will hydrolyze, or otherwise dissolve, while eluting the therapeutic agent. In yet another embodiment, the therapeutic composition, agent, or compound incorporated within the bioabsorbable material may vary in both composition and concentration. For example, the housing (26) may be constructed such that the initial eluted dosage of therapeutic composition, agent, or compound may be very high, with potency dropping off over time as a function of variable bioabsorption produced by using materials of varying bioabsorbability. In one embodiment, such variable elution may be utilized by constructing a housing (26) with multiple layers of therapeutic-loaded bioabsorbable materials, each layer having a different therapeutic concentration or each layer having a different rate of bioabsorbability or a combination of both.

Elution rates may also be varied by modifying the housing (26). For example, the housing (26) may include perforations (32) as illustrated in FIG. 7. The perforations (32) permit elution from the inner regions of the housing (26) or increase surface area of the housing (26). In one embodiment, elution rates may be controlled by overwrapping or encasing a housing (26) within a porous or semi-permeable covering material (34) as illustrated in FIG. 7. A porous expanded polytetrafluoroethylene material exhibits biocompatibility and substantial chemical inertness. A porous expanded polytetrafluoroethylene material for the overwrapping or encasing material is a preferred material.

Figure 6:
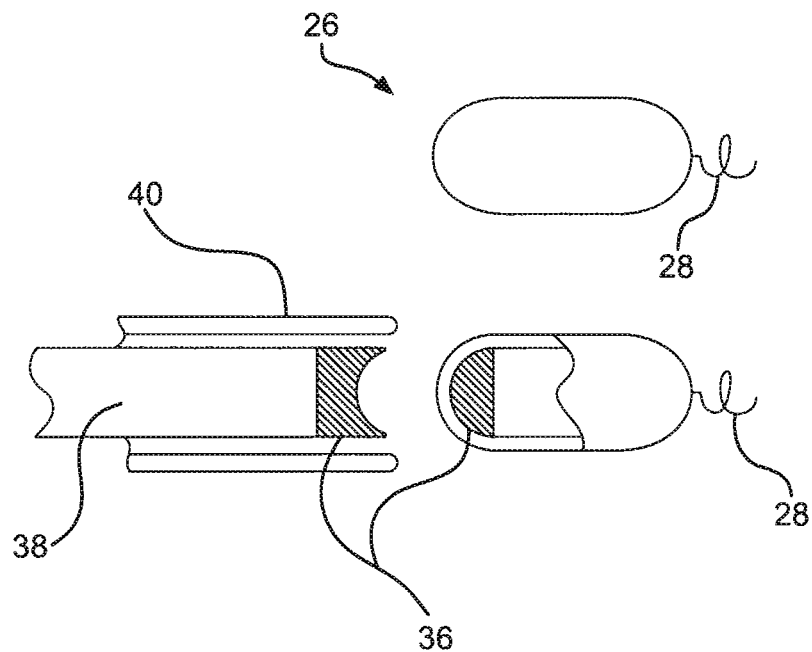
FIG. 6 illustrates a means for delivery or retrieval of the invention.

In some situations, it may be necessary to retrieve or replace an implanted embodiment of the present invention. Retrieval can be accomplished with a grasping tool. In one embodiment, magnetic attachment is used to retrieve or replace an implanted device (see e.g., FIG. 6). Magnets (36) may be embedded within or on the surface of the housing (26) and the associated catheter (38). The magnets (36) are configured exert an attractive force between the magnets. Once a sufficient magnetic attracting has been established, in-situ capture and movement of housing (26) can be effected. A sheath (40) may be used in the present invention. The sheath (40) is advanced over a housing (26) and the entire system rotated to cause release of the tissue attachment screw (28) and removal from the implant site.

Embodiments of the present invention may be configured for a variety of purposes, including therapeutic-eluting tips for cardiac pacing or Intracardiac Cardioverter Defibrillation (ICD), or neurostimulation leads; or other therapeutic-eluting devices for placement in proximity to other body tissues. Once placed at the desired location by interventional or surgical means and enclosed by tissue or affixed to tissue with an anchor, the invention can be of therapeutic value by locally or systemically delivering a drug. Although the left atrial appendage (30) implantation site is described herein, it should be appreciated the present invention may be applicable to a variety of other applications, such as the liver, kidney, brain, or peripheral vascular system. Accordingly, use of the present invention need not be constrained to the cardiovascular system. For instance, embodiments for implantation within a sinus cavity and loaded with an antihistamine or other allergy-symptom relieving agent are contemplated.

Figure 8A:
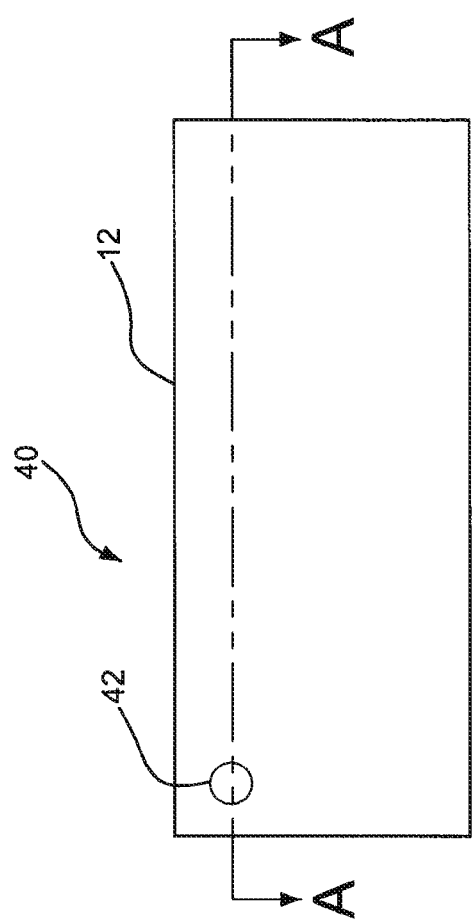
FIG. 8A illustrates an embodiment of the present invention.

FIG. 8A illustrates an embodiment of the present invention. Referring to FIG. 8A, therapeutic-releasing construction (40) is comprised of a biocompatible material, for example a coated film (10), a "capping layer" or impermeable material (12), and an opening (42) extending through impermeable material (12). Therapeutic-releasing construct (40) may be constructed to be any dimension but could be constructed to have a length of about 2 cm with a width of about 0.8 cm. The capping layer (12) may be of any thickness. A thickness of about 0.01 mm may be used. While shown as surrounding all of coated film (10), the capping layer (12) may surround only a portion of coated film (10). Coated film (10) may be of any thickness. A thickness of 0.5 mm may be used. Opening (42) may be formed by avoiding covering a portion of coated film (10) or by cutting through capping layer (12) by means as known in the art. Opening (42) may act as a diffusion barrier to further modulate release by providing a cover of permeable material over opening. Opening (42) may be of any dimension and shape. An opening (42) with the shape of a circle and the diameter of about 1 mm may be used. More than one opening may be used. The opening (42) may be placed at any location through impermeable material (12).

The rate at which therapeutic agents are released from therapeutic-releasing construction (40) will vary should the amount or dimensions of coated film (10) be varied, or the size or position of opening (42) be altered.

It will be understood that instead of using coated film (10) a therapeutic composition, agent, or compound, including one incorporated in a matrix, for example a polymer, could also be used in embodiments of the present invention.

Figure 8B:
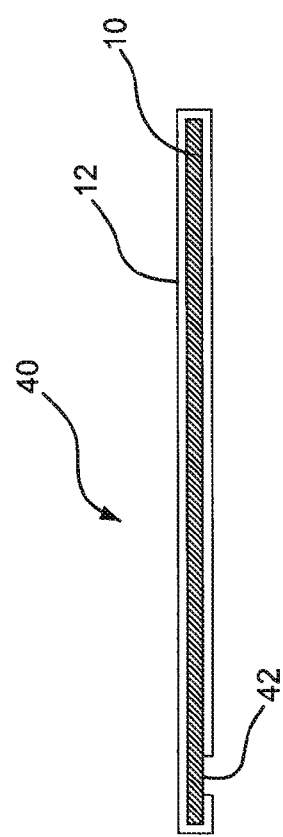
FIG. 8B illustrates a transverse cross section taken at the line "A" in FIG. 8A.

This embodiment is also illustrated in FIG. 8B as a transverse cross section taken at line "A" in FIG. 8A showing coated film (10) and capping layer material (12) and opening (42).

In practice, the embodiment illustrated in FIG. 8A-8B is a therapeutic-releasing construction or material (40) that may be applied to a variety of medical devices or used in vivo for therapeutic composition, agent, or compound delivery as discussed previously. If applied to a medical device, placement of the opening (42) may be manipulated to be in contact with tissue and/or fluid. Once in contact with tissue and/or fluid, the therapeutic composition, agent, or compound (not shown) contained within coated film (10) is preferentially eluted from those portions of the construction (40) not covered by material of the capping layer (12). In this embodiment, for example, the therapeutic composition, agent, or compound elutes or otherwise exits the invention from the illustrated opening (42). The therapeutic composition, agent, or compound in the coated film (10) may diffuse, or otherwise migrate, through portions of the coated film (10) covered by material of the capping layer (12) and exit the invention from uncovered and exposed areas of the coated film (10).

FIGS. 9A and 9B illustrate an embodiment of the present invention with FIG. 9B being a transverse cross section taken at line "B" in FIG. 9A. Referring to FIGS. 9A and 9B, therapeutic-releasing construction (50) is constructed as described for the embodiment in FIGS. 8A and 8B with a coated film (10), a "capping layer" or impermeable material (12), and an opening (42) extending through impermeable material (12). A barrier material (52) which may be impermeable or semi-permeable to the particular therapeutic composition, agent, or compound incorporated in coated film (10) is disposed within coated film (10). The height of barrier material (52) is shown in FIG. 9B as extending the full vertical distance between the capping layers (12) but may be dimensioned to extend only a portion of this distance. The width of barrier material (52) may be varied as well, as may the number of barriers (52).

In FIG. 9A (with upper capping layer (12) removed for clarity), barrier material (52) is shown extending from one edge of the coated film (10) toward a second edge and ending a distance away from said second edge. This distance alone or in combination with the number or dimensions of barrier materials (52) may be varied and can be used to tailor the transport or elution path of therapeutic agents through coated film (10) as is represented by a path of a theoretical molecule as illustrated in FIG. 9a as a dotted line with an arrow indicating the exit at the opening (42). Altering this elution pathway in any way may alter the elution rate of the therapeutic composition, agent, or compound. Elution pathways may also be altered by varying the orientation of the barrier material (52) as further illustrated in FIGS. 10-12.

In practice, the embodiment illustrated in FIG. 9A-9B may be used in vivo for therapeutic composition, agent, or compound delivery or applied to a substrate, for example a medical device as listed above.

Figure 10:
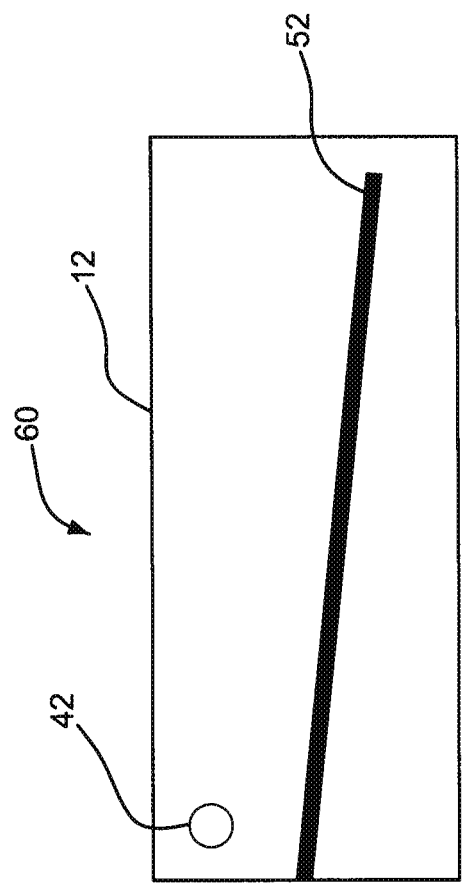
FIG. 10 illustrates an embodiment of the present invention.

FIG. 10 illustrates an embodiment of the present invention wherein the barrier material (52) has been positioned off the center line of therapeutic-releasing construction (60) and extending a longitudinal distance from one edge of coated film (10). Barrier (52) may also be placed at a location away from said edge. Any orientation of barrier material (52) may be employed. A barrier material (52) having an orientation of a non-zero angle off the longitudinal center line could be used. An orientation of about five degrees may also be used. As described previously, any length of barrier material (52) may be used. A length of barrier material (52) leaving about a 1 mm gap between the end of the barrier material (52) and edge of coated film (10) may also be used.

Depending on the shape, dimensions, and location of barrier materials (52), those portions of coated film (10) separated by barriers (52) may act as reservoirs for therapeutic compounds admixed or otherwise incorporated with coated film (10). Generally, the larger the volume of the separated portions of coated film (10) the more likely those portions are to serve as reservoirs. The smaller the volume the more likely the portions are to serve more as elution channels. When functioning as reservoirs, coated film volumes may contain different therapeutic compounds. For example in FIG. 10, the portion of coated film (10) above barrier (52) and proximate opening (42) could contain an anti-thrombogenic therapeutic and the lower portion of coated film (10) located below the barrier (52) could contain an anti-inflammatory. In use, the therapeutic-releasing construct (60) could be positioned proximate a vascular occlusion with the anti-thrombogenic therapeutic eluting, located nearest opening (42) eluting first to dissolve the occlusion and the anti-inflammatory eluting subsequently to lessen inflammation at the site of the lesion.

Figure 11:
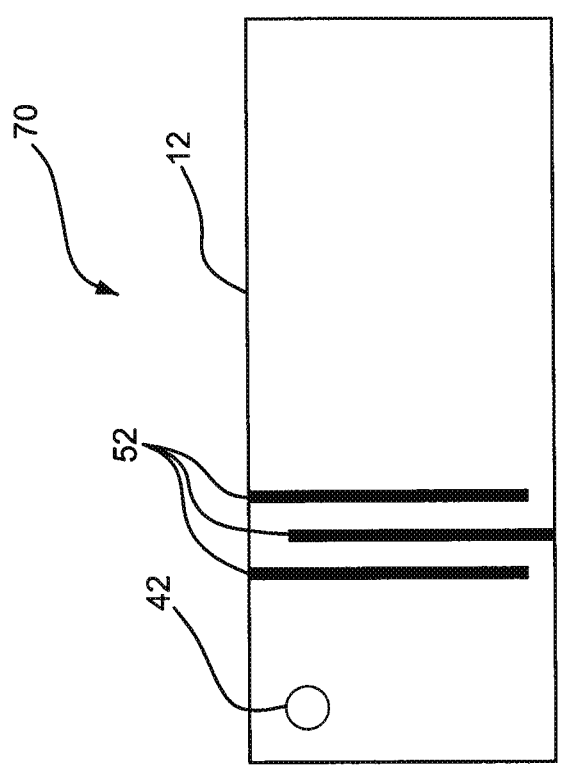
FIG. 11 illustrates an embodiment of the present invention.

FIG. 11 illustrates an embodiment of the present invention. FIG. 11 shows therapeutic-releasing construction (70) as previously described but with barrier materials (52) positioned perpendicular to the longitudinal center line of construction (70) and closer together than those shown in FIGS. 9A and 9B. This embodiment illustrates an elution pathway having these attributes: This embodiment provides a portion of therapeutic compound in close proximity to the hole with no barriers for a burst release followed by a longer release time for the majority of therapeutic compound contained beyond the barriers. The three barriers illustrated in FIG. 11 greatly extend the pathway for the therapeutic compound to travel. Moving the barriers closer to the hole will reduce the burst release of therapeutic compound and result in more therapeutic compound being released later in time. Having the barriers relatively close together results in a small amount of therapeutic compound between the barriers effectively creating two reservoirs. Spacing them further apart can create a four reservoir system as illustrated in FIG. 9A.

Figure 12:
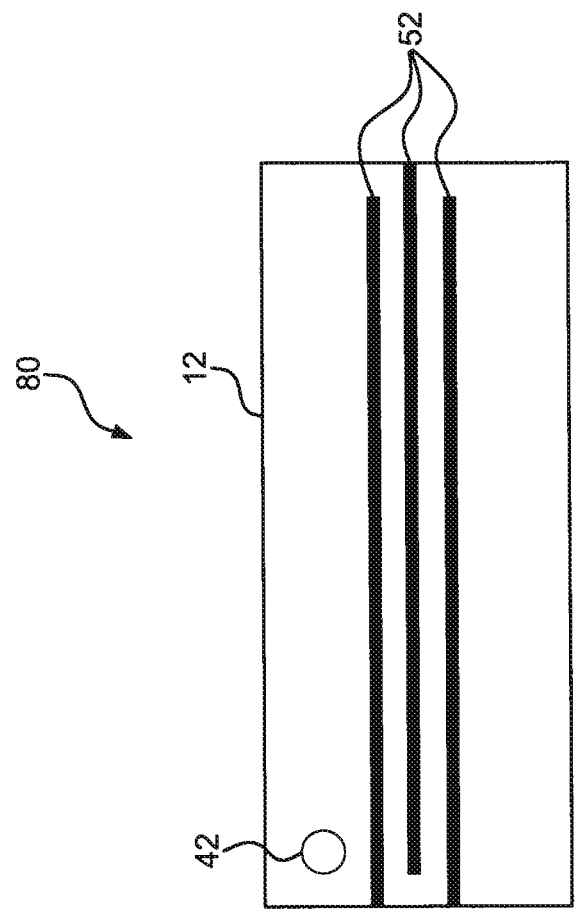
FIG. 12 illustrates an embodiment of the present invention.

FIG. 12 illustrates an embodiment of the present invention. FIG. 12 shows therapeutic-releasing construction (80) as previously described but with barrier materials (52) positioned parallel to the longitudinal center line of construction (70) and placed close to one another. This embodiment illustrates an elution pathway longer than those shown in FIGS. 9 through 11. In this embodiment, the therapeutic compound is released for the longest period of time, relative to the other constructions. As previous described the amount of therapeutic compound released earlier or later can be tailored by moving the barriers closer or further away from the hole, respectively. Spacing the barriers further apart will alter the size of areas of the coated film (10) serving as therapeutic agent reservoirs.

Figure 13:
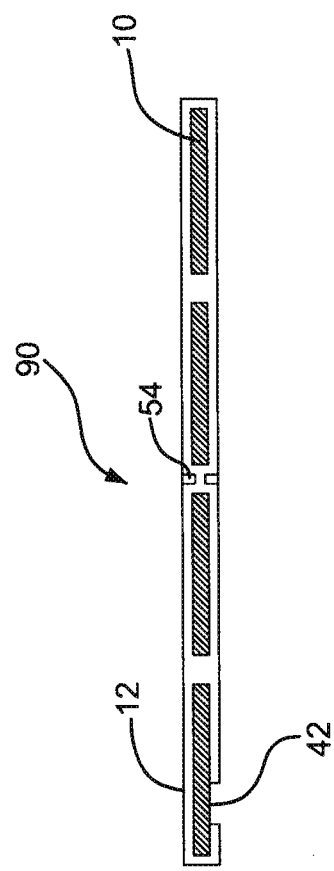
FIG. 13 illustrates an embodiment of the present invention.

FIG. 13 shows a cross section of therapeutic-releasing construct (90) as previously described but barriers (54) have been created by fusing a portion of the opposing capping layers (12) together after removing coating film (10). This construct may be achieved by using various methods known in the art. For example, coated film (10) may be placed on the capping layer (12) which includes outlet (42). Then desired portions of the coated film (10) are removed, for example with a laser. Then capping layers (12) are added to all edges of therapeutic-releasing construct (90) and a capping layer (12) is added to the top of the construct, opposite the capping layer (12) with hole (42). The construct (90) is then placed into a die which presses a portion of the opposing capping layers (12) together, fusing them to create an impermeable barrier (54). In addition to pressure, the fusing together of portions of the capping layers (12) may be augmented by application of heat or adhesives to the areas where coated film (1) has been previously removed. It will be understood that the shape and dimensions of impermeable barrier (54) can be varied to achieve the desired eluting pathway(s).

EXAMPLES

Example 1

A copolymer of tetrafluoroethylene/perfluoromethylvinylether (TFE/PMVE) as described in EP 1545642 B1 was obtained in a 0.12 wt % solution of Fluorinert FC-77 (3M, St Paul, Minn.). To this solution was added an appropriate amount of dexamethasone sodium phosphate (Pharmacia & Upjohn Company, Kalamazoo Mich.) to produce a solution of 0.12 wt % of the drug. The solution was sonicated to ensure complete mixing.

An expanded polytetrafluoroethylene (ePTFE) film tape of approximately 0.01 mm in thickness and 0.8 cm width was utilized in the manufacturing of the drug release system. A length of ePTFE film tape approximately 8 cm long was mounted onto a flat sheet of aluminum foil with a section of adhesive tape at each end. The ePTFE film tape was spray-coated with the TFE/PMVE and dexamethasone sodium phosphate solution using an airbrush (Badger standard set, model 350 (Badger Air Brush Co., Franklin Park, Ill.) set at 220 KPa gauge air pressure. Spray coating was conducted for 2-3 minutes, the coating was allowed to air dry, and the coated film then coated again. This was continued until the coating mass added to the tape was approximately 1 mg per 1 cm length. The opposite side of the film tape was left uncoated.

A metal tube of outside diameter of 1.50 mm, length 3 cm was obtained. A thin layer of a substantially non-porous composite film including expanded polytetrafluoroethylene (ePTFE) with a thermal adhesive layer of ethylene fluoroethylene perfluoride on one side was applied to the tube extending approximately 0.8 cm back from the tip of one end. This construction was utilized as a model cardiac pacing lead tip. The end of a segment of the coated film tape of 0.8 cm width and 2 cm in length was attached to the outer circumference of the tube, with the drug coated side facing the tube, at its end utilizing a silicone adhesive (MED-137, NuSil Technology, Carpinteria Calif.) and allowed to fully cure. After curing, a spatula was used to spread a thin film of the silicone adhesive on the coated side of the coated tape, and the tape was wrapped with the coated side toward the tube. The wrapped coated tape was then capped on a portion of its outer surface using silicone applied with a spatula, while not coating a thin strip of approximately 1 mm or less in width adjacent to the opening of the coated tape wrapped metal tube. The construction was allowed to cure overnight.

Constructions so made possessed a theoretical drug loading of approximately 2 mg and were tested for determination of drug release. A construction was placed in a vial containing 3 ml of PBS and maintained in a 37 degree C. incubator. Samples of 3 ml were taken at various time points and the vial replenished with fresh PBS to maintain the volume at 3 ml. Drug concentration was measured on an UV spectrophotometer at 242 nm. The graph shown in FIG. 4 demonstrates an extended elution time for the drug dexamethasone sodium phosphate.

The invention claimed is:

1. A therapeutic-releasing material disposed on a substrate comprising:
   a first biocompatible polymeric material having a therapeutic agent incorporated in at least a portion thereof and adjacent the substrate;
   a second biocompatible polymeric material having a first surface and a second surface, wherein the first biocompatible polymeric material is incorporated into at least a portion of said first surface;
   an impermeable capping layer surrounding at least a portion of an outer surface of the first biocompatible material;
   a biocompatible polymeric barrier disposed within said first biocompatible polymeric material and having a height such that said barrier extends a full vertical distance between the impermeable capping layer and the substrate,
   wherein said barrier is substantially impermeable to said therapeutic agent;
   at least one formed opening having a dimension and a location and extending through the impermeable capping layer; and
   said barrier is structured with a length such that said barrier extends from a first edge of the first biocompatible polymeric material towards a second edge of the first biocompatible polymeric material, and ends a predetermined distance away from the second edge.

2. The therapeutic-releasing material of claim 1 further comprising a plurality of formed openings in said impermeable capping layer, wherein the therapeutic agent release rate is at least partially determined by at least one of a dimensions, location, and number of said plurality of formed openings.

3. The therapeutic-releasing material of claim 1 wherein said second biocompatible polymeric material comprises a fluoropolymer composition.

4. The therapeutic-releasing material of claim 3 wherein said fluoropolymer is porous polytetrafluoroethylene.

5. The therapeutic-releasing material of claim 1 wherein said biocompatible polymeric barrier is a silicone composition.

6. The therapeutic-releasing material of claim 1 wherein said therapeutic agent is dexamethasone sodium phosphate.

7. The therapeutic-releasing material of claim 1 wherein said therapeutic agent release rate is further determined by said first biocompatible polymeric material.

8. The therapeutic-releasing material of claim 1 wherein said second biocompatible polymeric material is a film.

9. The therapeutic-releasing material of claim 1 wherein said substrate is at least a portion of a cardiac pacing lead.

10. The therapeutic-releasing material of claim 1 wherein said therapeutic-releasing material is wrapped at least once around said substrate material.

11. The therapeutic-releasing material of claim 10 wherein said wrapped therapeutic-releasing material has a spiral configuration.

12. The therapeutic-releasing material of claim 1 wherein said substrate is at least a portion of a cardiac pacing lead.

13. A cardiac pacing lead comprising:
   a cardiac pacing lead element having a proximal end and a distal end;
   an electrically conductive connector at said proximal end;
   an electrode located at said distal end;
   at least one electrically conductive element connecting said connector to said electrode; and
   at least a portion of said cardiac pacing lead element covered with a therapeutic-releasing material comprising:
      a first biocompatible polymeric material having a therapeutic agent incorporated in at least a portion thereof and adjacent the cardiac pacing lead element;
      a second biocompatible polymeric material having a first surface and a second surface, wherein the first biocompatible polymeric material is incorporated into at least a portion of said first surface;
      an impermeable capping layer surrounding at least a portion of an outer surface of the first biocompatible material and having at least one formed opening having a dimension and a location and extending through impermeable capping layer; and
      a plurality of biocompatible polymeric barriers disposed within said first biocompatible polymeric material and having a height such that each of said plurality of biocompatible polymeric barriers extends a full vertical distance between an inner surface and the outer surface of the first biocompatible material,
   wherein said plurality of biocompatible barriers are substantially impermeable to said therapeutic agent; and
   each of said plurality of biocompatible polymeric barriers is positioned parallel to a longitudinal center line of the therapeutic-releasing material, and each of said plurality of biocompatible polymeric barriers has a length such that each of said plurality of biocompatible polymeric barriers extends from a first edge of the first biocompatible polymeric material towards a second edge of the first biocompatible polymeric material, and ends a predetermined distance away from the second edge.

14. The cardiac pacing lead of claim 13 wherein the therapeutic agent release rate is at least partially determined by at least one of the dimension and location of said at least one formed opening.

15. The cardiac pacing lead of claim 13 wherein said second biocompatible polymeric material comprises a fluoropolymer composition.

16. The cardiac pacing lead of claim 15 wherein said fluoropolymer is porous polytetrafluoroethylene.

17. The cardiac pacing lead of claim 13 wherein said plurality of biocompatible polymeric barriers are a silicone composition.

18. The cardiac pacing lead of claim 13 wherein said therapeutic agent is dexamethasone sodium phosphate.

19. The cardiac pacing lead of claim 13 further comprising a plurality of formed openings in said impermeable capping layer, wherein the therapeutic agent release rate is at least partially determined by at least one of the dimensions, location, and number of said plurality of formed openings.

20. A therapeutic releasing material comprising
a first biocompatible polymeric material having a surface and having a therapeutic agent disposed on the surface, wherein an elution pathway extends along at least a section of the surface;
an impermeable capping layer covering all of said first biocompatible material except for a location of an opening extending through the impermeable capping layer and in communication with said elution pathway; and
a biocompatible polymeric barrier disposed within said first biocompatible polymeric material and having a height such that said barrier extends a full vertical distance between the impermeable capping layer covering an inner surface of the first biocompatible material and the impermeable capping layer covering an outer surface of the first biocompatible material.

21. The therapeutic-releasing material of claim 20, wherein a therapeutic agent release rate is at least partially determined by at least one of dimension and location of said opening.

* * * * *